(12) United States Patent
Hanada et al.

(10) Patent No.: US 6,384,174 B2
(45) Date of Patent: May 7, 2002

(54) FLUORINE-CONTAINING DIOLS AND USE THEREOF

(75) Inventors: Kazuyuki Hanada; Kazuya Kimura, both of Tokyo (JP)

(73) Assignees: Dainichiseika Color & Chemicals Mfg. Co., Ltd.; Ukima Colour & Chemicals Mfg. Co., Ltd., both of Tokyo (JP)

( * ) Notice: Subject to any disclaimer, the term of this patent is extended or adjusted under 35 U.S.C. 154(b) by 0 days.

(21) Appl. No.: 09/799,029

(22) Filed: Mar. 6, 2001

(30) Foreign Application Priority Data

Mar. 7, 2000 (JP) .......................................... 2000-062226

(51) Int. Cl.⁷ ............................................... C08G 18/30
(52) U.S. Cl. ............................. 528/70; 528/28; 560/25; 560/115; 560/158; 252/182.15
(58) Field of Search ........................ 560/25, 115, 158; 528/70, 28; 252/182.15

(56) References Cited

U.S. PATENT DOCUMENTS

| | | |
|---|---|---|
| 4,347,338 A | 8/1982 | Torii et al. |
| 4,746,684 A | 5/1988 | Kuriyama et al. |
| 4,853,418 A | 8/1989 | Hanada et al. |
| 4,942,212 A | 7/1990 | Hanada et al. |
| 5,945,185 A | 8/1999 | Hirai et al. |

OTHER PUBLICATIONS

U.S. application No. 09/801,739, filed Mar. 9, 2001, pending.
U.S. application No. 09/813,208, filed Mar. 21, 2001, pending.
U.S. application No. 09/799,029, filed Mar. 6, 2001, pending.

*Primary Examiner*—Rachel Gorr
(74) *Attorney, Agent, or Firm*—Oblon, Spivak, McClelland, Maier & Neustadt, P.C.

(57) ABSTRACT

Fluorine-containing diols represented by the following formula are provided:

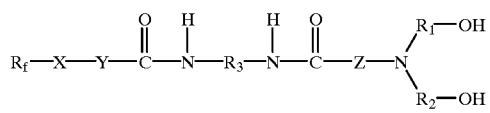

wherein $R_f$ represents a perfluoroalkyl or perfluoroalkenyl group having 1 to 20 carbon atoms; X represents a substituted or unsubstituted alkylene group having 1 to 10 carbon atoms, a substituted or unsubstituted alkenylene group represented by $—CH=CH—(CH_2)_n—$ in which n is from 1 to 10, or

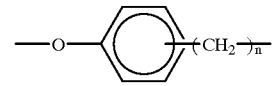

in which n is from 0 to 6; Y represents a direct bond, —O—, —NH—, or —$R_0$—NH— in which $R_0$ is an alkylene group having 1 to 6 carbon atoms; Z represents a direct bond or —N(R')R— in which R is an alkylene group having 1 to 20 carbon atoms and R' is a hydrogen atom or an alkyl group having 1 to 6 carbon atoms; $R_1$ and $R_2$ divalent organic groups; and $R_3$ represents a residual group of diisocyanate. These diols are useful for polyurethanes.

16 Claims, 2 Drawing Sheets

FLUORINE-CONTAINING DIOLS AND USE THEREOF

BACKGROUND OF THE INVENTION a) Field of the Invention

This invention relates to novel diols containing a perfluoroalkyl group or perfluoroalkenyl group, which will hereinafter be commonly abbreviated as an "$R_f$ group", and also to polyurethanes using the diols.

b) Description of the Related Art

Polyurethane is excellent not only in abrasion resistance, adhesion properties, flexibility, chemical resistance and the like but also in applicability to various molding or forming processes. Polyurethane are, therefore, widely used as binders in various coating materials, paints, inks and the like and also as raw materials for films, sheets and other molded or formed products. A wide range of polyurethanes suited for individual applications have been proposed. It is to be noted that the term "polyurethane" as used herein collectively mean "polyurethane", "polyurea" and "polyurethane-polyurea".

These polyurethanes are each obtained basically by reacting a polyol and/or a polyamine, a polyisocyanate and optionally, a chain extender, and depending on the kinds and combinations of these individual components, polyurethanes of various physical properties can be provided.

As one of such processes, it has been proposed to introduce an organic fluorine compound into a molecule of polyurethane by copolymerization so that the polyurethane is imparted with properties of the organic fluorine compound, such as water repellency and oil repellency, non-tackiness, abrasion resistance and anti-fouling property, while retaining its inherent good properties. For example, processes have been proposed for the production of fluorine-containing polyurethane, which make combined use of a one-end diol having an $R_f$ group (the term "one-end diol" as used herein means "a compound having two hydroxyl groups at only one end of its molecule") and a conventional diol other than the one-end diol (diols other than one-end diols will hereinafter be referred to simply as "diols") (JP S43-26518 B, JP S61-252220 A).

As a conventional process for the preparation of a one-end diol having an $R_f$ group, a process which, for example, proceeds following such a reaction scheme as will be described next is known.

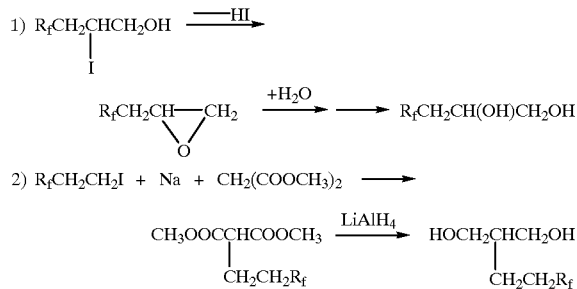

As is appreciated from the foregoing, the conventional processes for the preparation of one-end diols having the $R_f$ group all require many steps. The one-end diols having the $R_f$ group, which are obtained as high-purity products, are costly, so that these conventional processes have a problem in their practical use on an industrial scale.

In conventional polyurethanes each of which is available from combined use of a one-end diol having the $R_f$ group and a diol, on the other hand, any attempt to make the polyurethanes exhibit functions of fluorine by increasing the contents of fluorine in the polyurethanes leads to reductions in certain inherent properties of the polyurethanes such as rubber elasticity and mechanical strength.

This is attributed to properties of the $R_f$ groups that the resulting fluorine-containing polyurethane molecules are stiff and tend to orient in a particular direction because fluorine atoms are very bulky, produce strong repulsion therebetween and are closely packed in the molecules so that the molecular chains are hardly bendable. As a result, polyurethane is considered to be reduced in rubber elasticity due to a decrease in the thermal motion of soft segments in the molecular chains due to the $R_f$ groups and/or to be reduced in strength due to inhibition to aggregation of hard segments.

The above-mentioned problem of polyurethanes in each of which a conventional one-end diol having an $R_f$ group has been introduced is caused by strong effects of the $R_f$ group on the polyurethane backbone as the $R_f$ group and the polyurethane backbone are located close to each other.

SUMMARY OF THE INVENTION

An object of the present invention is, therefore, to provide an $R_f$-containing one-end diol, which can be prepared with high purity at low cost by simple steps, as a substitute for the conventional $R_f$-containing one-end diols each of which causes such a problem as mentioned above when employed as a diol component for polyurethane. Another object of the present invention is to provide a process for the preparation of the $R_f$-containing one-end diol. A further object of the present invention is to provide a novel $R_f$-containing polyurethane imparted with excellent water repellency and oil repellency, anti-fouling property, abrasion resistance, non-tackiness and the like without reductions in the inherent good properties of polyurethane.

The above-described objects can be achieved by the present invention as will be described hereinafter.

In one aspect of the present invention, there is thus provided a fluorine-containing diol represented by the following formula (I):

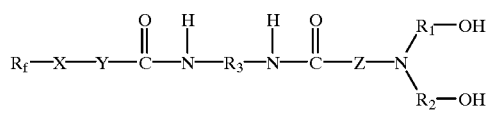

wherein $R_f$ represents a perfluoroalkyl or perfluoroalkenyl group having 1 to 20 carbon atoms; X represents a substituted or unsubstituted alkylene group having 1 to 10 carbon atoms, a substituted or unsubstituted alkenylene group represented by —CH=CH—(CH$_2$)$_n$— in which n stands for an integer of from 1 to 10, or

in which n stands for an integer of from 0 to 6; Y represents a direct bond, —O—, —NH—, or —R$_0$—NH— in which R$_0$ is an alkylene group having 1 to 6 carbon atoms; Z represents a direct bond or —N(R')R— in which R is an alkylene group having 1 to 20 carbon atoms and R' is a hydrogen atom or an alkyl group having 1 to 6 carbon atoms;

$R_1$ and $R_2$ each independently represent a divalent organic group; and $R_3$ represents a residual group of an aliphatic, alicyclic or aromatic diisocyanate.

In another aspect of the present invention, there is also provided a process for the preparation of a fluorine-containing diol represented by the above-described formula (I), which comprises reacting a fluorine-containing compound, which has an $R_f$ group and an active-hydrogen-containing group, with a diisocyanate at an NCO/OH ratio of approximately 2, and then reacting a resulting fluorine-containing group, which contains one free isocyanate group in a molecule, with a dialkanolamine at a temperature not higher than 50° C.

In a further aspect of the present invention, there is also provided a fluorine-containing polyurethane obtained by reacting a fluorine-containing diol represented by the above-described formula (I), an aliphatic, aromatic or alicyclic diisocyanate, and an aliphatic, aromatic or alicyclic diol and/or a diamine, and optionally, a chain extender; the polyurethane having fluorine-containing side chains, which are represented by the following formula (II):

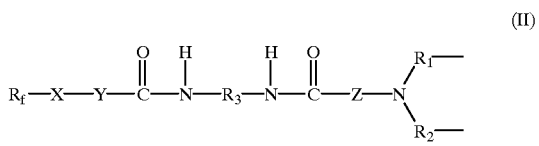

(II)

wherein $R_1$ to $R_3$, $R_f$, X, Y and Z have the same meanings as defined claim 1
and which are bonded via $R_1$ and $R_2$ thereof to a backbone of the polyurethane by means of urethane bonds and/or urea bonds, at a content such that the polyurethane has a fluorine content of from 3 to 80 wt. %; and the polyurethane having a weight average molecular weight of from 5,000 to 500,000.

In a still further aspect of the present invention, there is also provided a fluorine-containing polyurethane as described above, which further comprises polysiloxane segments derived from a polysiloxane having at least one active-hydrogen-containing group.

In a still further aspect of the present invention, there is also provided a process for the production of a fluorine-containing polyurethane, which comprises reacting a fluorine-containing diol represented by the above-described fluorine-containing diol represented by the above-described formula (I), a diisocyanate, and a diol other than the fluorine-containing diol and/or a diamine, and optionally a chain extender.

In a still further aspect of the present invention, there is also provided a process for the production of a fluorine-containing polyurethane as described above, which comprises further reacting a polysiloxane having at least one active-hydrogen-containing group in an amount such that a content of polysiloxane segments in the polyurethane falls within a range of from 1 to 75 wt. %.

These novel polyurethanes obtained from the $R_f$-containing diol are excellent in surface properties—such as water repellency and oil repellency, anti-fouling property, abrasion resistance and non-tackiness—while retaining inherent good properties of polyurethane such as strength characteristics, rubber elasticity and low-temperature characteristics more sufficiently than polyurethanes making use of conventional $R_f$-containing diols.

DETAILED DESCRIPTION OF THE INVENTION AND PREFERRED EMBODIMENTS

Figure 1:
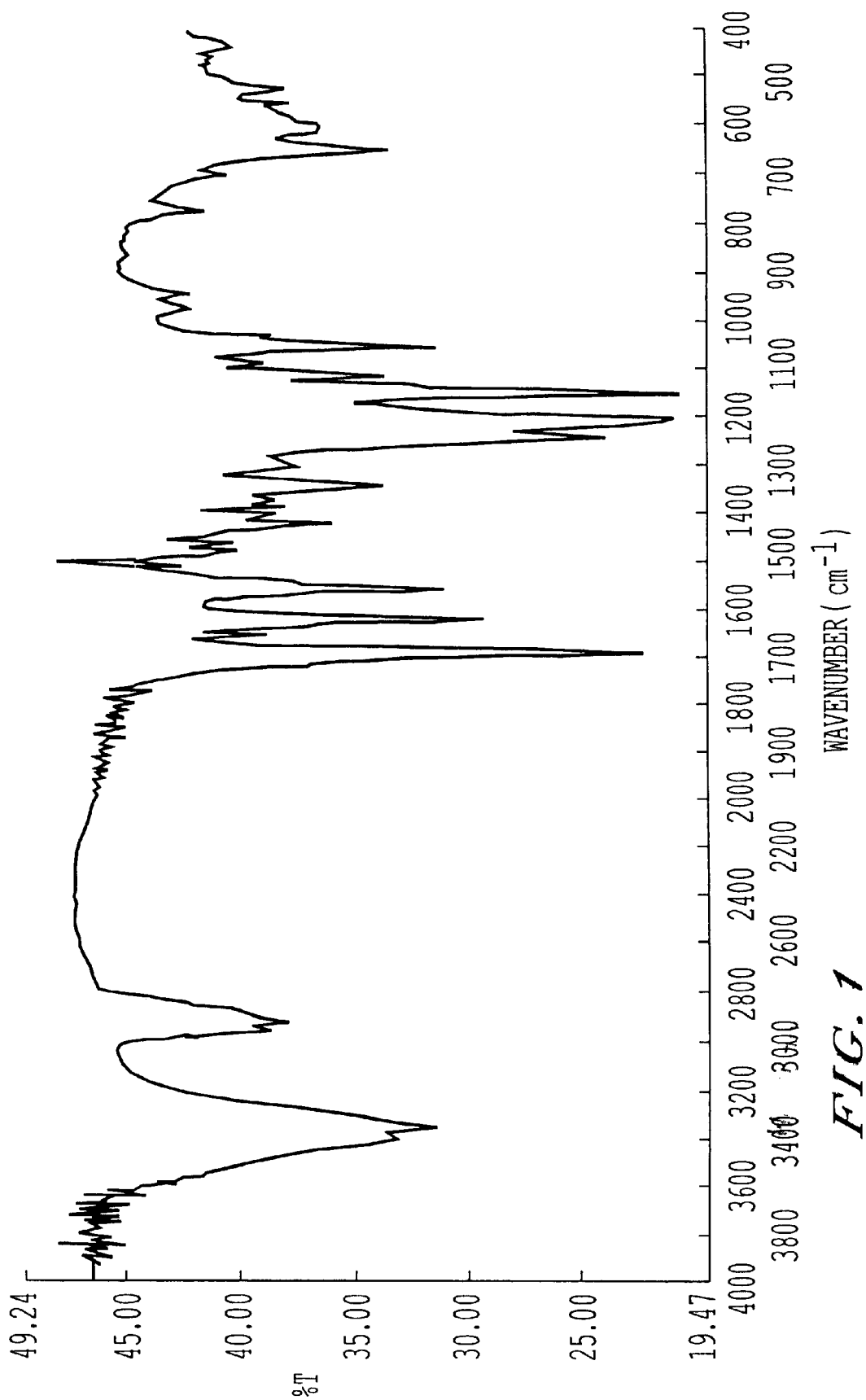
FIG. 1 is an infrared absorption spectrum of a fluorine-containing diol of Example 1.

The present invention will hereinafter be described in further detail based on certain preferred embodiments.

The $R_f$-containing one-end diol according to the present invention, which is represented by the above-described formula (I), can be prepared, for example, by the following steps:

a) Firstly, a fluorine-containing compound (1) having an active-hydrogen-containing group (for example, a hydroxyl group) and a diisocyanate (2) are reacted at an NCO/OH ratio of approximately 2 to obtain a fluorine-containing compound (3) having one free isocyanate group in its molecule.

b) Using a difference in the reactivity to an isocyanate group between an amino group and a hydroxyl group, the fluorine-containing compound (3) and a dialkanolamine (4) are then reacted at a temperature not higher than 50° C. such that the isocyanate group and the amino group are selectively reacted to obtain an $R_f$-containing one-end diol represented by the following formula (A).

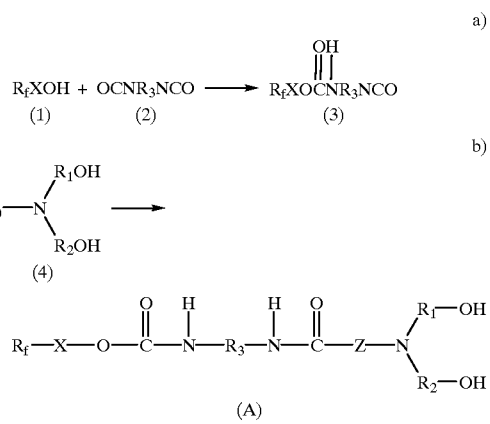

wherein $R_f$, $R_1$ to $R_3$, X and Z have the same meanings as defined above, and $Z_0$ represents H or an alkylamino group having 1 to 20 carbon atoms and a single primary or secondary amino group at an end thereof.

Examples of fluorine-containing compounds usable in the present invention can include the following compounds:

(1) Alcohol type $F(CF_2)_m(CH_2)_nOH$ (m = 1–12, n = 1–6)

$\begin{array}{c}CF_3\\ \diagdown\\ \phantom{CF_3}CF(CF_2)_m(CH_2)_nOH\\ \diagup\\ CF_3\end{array}$ (m = 0–10, n = 1–6)

$\begin{array}{c}CF_3\\ \diagdown\\ \phantom{CF_3}CF(CF_2)_mCH_2CHI(CH_2)_nOH\\ \diagup\\ CF_3\end{array}$ (m = 0–10, n = 1–6)

$H(CF_2)_m(CH_2)_nOH$ (m = 1–12, n = 1–6)

-continued $F(CF_2)_mO$—⟨phenyl⟩—$(CH_2)_nOH$  (m = 1–12, n = 0–6)

$\begin{array}{c}CF_3\\ \phantom{x}\\ CF_3\end{array}\!\!\!\!\!>\!CF(CF_2)_mO$—⟨phenyl⟩—$(CH_2)_nOH$  (m = 0–10, n = 0–6)

(2) Epoxy type $F(CF_2)_m(CH_2)_nCH\!-\!\!-\!\!CH_2$  (m = 1–12, n = 1–6)
   \O/

$\begin{array}{c}CF_3\\ \phantom{x}\\ CF_3\end{array}\!\!\!\!\!>\!CF(CF_2)_m(CH_2)_nCH\!-\!\!-\!\!CH_2$  (m = 0–10, n = 1–6)
   \O/

$H(CF_2)_m(CH_2)_nO(CH_2)_pCH\!-\!\!-\!\!CH_2$  (m = 1–12, n,p = 1–6)
   \O/

The above-described epoxy compounds are each used after introducing a terminal hydroxyl group therein by a reaction with an active-hydrogen-containing compound such as a polyol, a polyamide or a polycarboxylic acid.

(3) Amine type $F(CF_2)_m(CH_2)_nNH_2$  (m = 1–12, n = 1–6)

$\begin{array}{c}CF_3\\ \phantom{x}\\ CF_3\end{array}\!\!\!\!\!>\!CF(CF_2)_m(CH_2)_nNH_2$  (m = 0–10, n = 1–6)

$F(CF_2)_mO$—⟨phenyl⟩—$(CH_2)_nNH_2$  (m = 1–12, n = 0–6)

$\begin{array}{c}CF_3\\ \phantom{x}\\ CF_3\end{array}\!\!\!\!\!>\!CF(CF_2)_mO$—⟨phenyl⟩—$(CH_2)_nNH_2$  (m = 0–10, n = 0–6)

(4) Carboxylic acid type $F(CF_2)_m(CH_2)_nCOOH$  (m = 1–12, n = 0–6)

$\begin{array}{c}CF_3\\ \phantom{x}\\ CF_3\end{array}\!\!\!\!\!>\!CF(CF_2)_m(CH_2)_nCOOH$  (m = 0–10, n = 0–6)

The above-listed fluorine-containing compounds, each of which has an active-hydrogen-containing group, are examples of compounds preferred for use in the present invention, and in the present invention, the fluorine-containing compound shall not be limited to these exemplified ones. In the present invention, it is therefore possible to use not only the above-exemplified fluorine-containing compounds but also known fluorine-containing compounds presently sold on the market and available from the market. Fluorine-containing compounds particularly preferred in the present invention are the above-exemplified fluorine-containing compounds of the alcohol type.

As the diisocyanate for use in the present invention, any diisocyanate known to date is usable, and no particular limitation is imposed thereon. Preferred usable examples can include aromatic diisocyanates such as toluene-2,4-diisocyanate, 4-methoxy-1,3-phenylene diisocyanate, 4-isopropyl-1,3-phenylene diisocyanate, 4-chloro-1,3-phenylene diisocyanate, 4-butoxy-1,3-phenylene diisocyanate, 2,4-diisocyanatodiphenyl ether, 4,4'-methylenebis(phenylisocyanate) (MDI), durylene diisocyanate, tolidine diisocyanate, xylylene diisocyanate (XDI), 1,5-naphthalene diisocyanate, benzidine diisocyanate, o-nitrobenzidine diisocyanate, and 4,4-diisocyanatodibenzyl; aliphatic diisocyanates such as methylene diisocyanate, 1,4-tetramethylene diisocyanate, 1,6-hexamethylene diisocyanate, and 1,10-decamethylene diisocyanate; alicyclic diisocyanates such as 1,4-cyclohexylene diisocyanate, 4,4-methylene-bis (cyclohexylisocyanate), 1,5-tetrahydronaphthalene diisocyanate, isophorone diisocyanate, hydrogenated MDI, and hydrogenated XDI; and obviously, polyurethane prepolymers obtained by reacting these diisocyanates with polyols or polyamines of low molecular weights such that the resulting prepolymers have isocyanate groups at ends thereof.

Examples of dialkanolamines usable in the present invention can include compounds represented by the following formula:

$$Z_0-N\!\!\begin{array}{c}R_1OH\\ \\ R_2OH\end{array}$$

wherein $R_1$, $R_2$ and $Z_0$ have the same meanings as defined above, and preferably, $R_1$ and $R_2$ may each independently represent a divalent group having 2 to 12 carbon atoms and containing an aliphatic, alicyclic or aromatic ring, and the divalent group may contain one or more O, N and/or S atoms therein.

Preferred examples can include diethanolamine, dipropanolamine, dihexanolamine, 1-aminopropane glycol, diethanolaminomethylamine, diethanolaminoethylamine, and diethanolaminopropylamine.

A more specific description will now be made about the preparation process of the $R_f$-containing diol represented by the formula (I).

Firstly, a fluorine-containing compound, which has an active-hydrogen-containing group, and a diisocyanate are reacted at an equivalent ratio such that the reaction product contains one free isocyanate group in a molecule (NCO/OH≈2), in a solventless manner or in an organic solvent, in the presence or absence of a conventional polymerization catalyst for polyurethanes (for example, an organometal compound, a tertiary amine or the like), and at 0 to 150° C., preferably 20 to 90° C.

At a temperature of 50° C. or lower, preferably 40° C. or lower, more preferably 30° C. or lower, the above-described fluorine-containing compound having one free isocyanate group is then added dropwise into the above-described dialkanolamine.

Under these conditions, an isocyanate group selectively reacts with an amino group before a hydroxyl group [Ann. Chem., 562, 205 (1949)], whereby an $R_f$-containing one-end diol represented by the formula (I) according to the present invention is obtained and at low temperatures, a portion of the reaction product progressively precipitates as crystals in an organic solvent as the reaction proceeds. After completion of the reaction, the reaction mixture is poured into a poor solvent such as water, toluene, xylene or n-hexane to cause precipitation of the reaction product as crystals.

Unreacted diisocyanate and dialkanolamine can be eliminated by washing the precipitated crystals with a poor solvent (an aromatic or aliphatic hydrocarbon) at room temperature. The $R_f$-containing one-end diol represented by the formula (I) can, therefore, be obtained with high purity.

The fluorine-containing polyurethane according to the present invention can be obtained by reacting the $R_f$-containing diol, which is represented by the formula (I) and has been obtained by the above-described reaction, with the above-described diisocyanate and also with the diol and/or diamine.

As the diol, diols which have been used to date for the production of polyurethane are all usable, and no limitation is imposed thereon. Illustrative are glycols of low molecular weight such as ethylene glycol, 1,2-propylene glycol, 1,3-propylene glycol, 1,4-butylene glycol, and 1,6-hexamethylene glycol; polyester diols obtained from dibasic acids, such as adipic acid, maleic acid and terephthalic acid, and glycols; polyester diols such as polylactones obtained by subjecting lactones to ring-opening polymerization with glycols; polycarbonate diols; and polyether diols such as polytetramethylene glycol, polyethylene glycol, and polypropylene glycol.

As the diamine, diamines which have been used to date for the production of polyurethane are all usable, and no particular limitation is imposed thereon. Illustrative are aliphatic diamines such as methylenediamine, ethylenediamine, trimethylenediamine, hexamethylenediamine, and octamethylenediamine; aromatic diamines such as phenylenediamine, 3,3'-dichloro-4,4'-diaminodiphenyl ether, 4,4'-methylenebis(phenyl)amine, 4,4'-diaminodiphenyl ether, and 4,4'-diaminodiphenylsulfone; and alicyclic diamines such as cyclopentadiamine and cyclohexyldiamine. Examples of the chain extender can include the above-described diols and diamines of low molecular weight. Chain extenders which have been used to date for the production of polyurethane are all usable, and no particular limitation is imposed thereon.

Using these components and a conventional process known for the production of polyurethane, the fluorine-containing polyurethane according to the present invention can be obtained. The process according to the present invention for the production of polyurethane comprises reacting the $R_f$-containing diol represented by the formula (I), the diisocyanate, the diol and/or diamine, and optionally, the chain extender. No particular limitation is imposed on the reaction conditions. Further, no particular limitation is imposed either on the reaction method, and the reaction can be performed by any method such as bulk polymerization, solution polymerization or dispersion polymerization. Moreover, a suitable combination of a diol, a diamine and a diisocyanate can be chosen depending on the application purpose and performance requirements of a target fluorine-containing polyurethane, and no particular limitation is imposed on them.

As another embodiment of the present invention, there is also provided a fluorine-containing polyurethane which further contains polysiloxane segments, which have been derived from a polysiloxane having at least one active-hydrogen-containing group, in an amount such that the content of polysiloxane segments in the polyurethane molecule falls within a range of from 1 to 75 wt. %.

The polysiloxane for use in the present invention has at least one active-hydrogen-containing group, for example, at least one amino group, epoxy group, hydroxyl group, mercapto group, carboxyl group or like group. Preferred examples of such a polysiloxane can include the following compounds.

(1) Amino-modified polysiloxanes (1) Amino-modified polysiloxanes

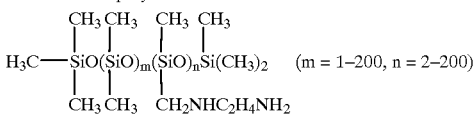

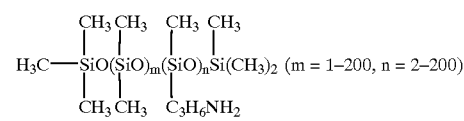

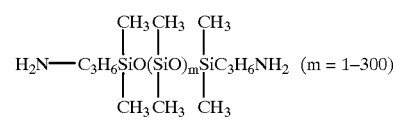

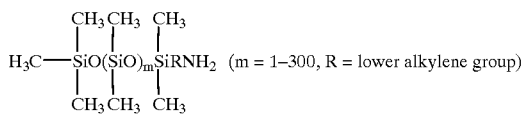

(2) Epoxy-modified polysiloxanes

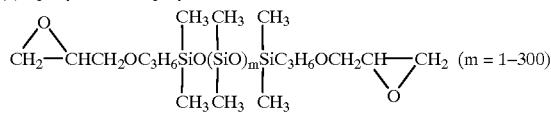

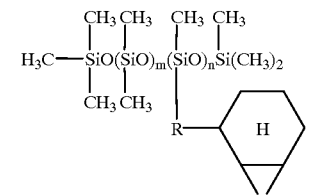

(m = 1–200), n = 2–200, R = lower alkylene group)

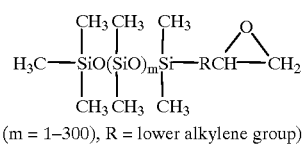

(m = 1–300), R = lower alkylene group)

(3) Alcohol-modified polysiloxanes

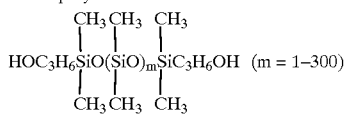

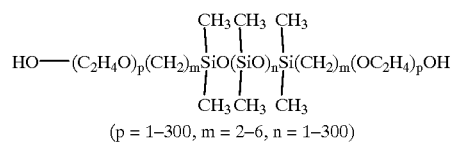

(p = 1–300, m = 2–6, n = 1–300)

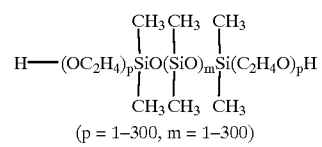

(p = 1–300, m = 1–300)

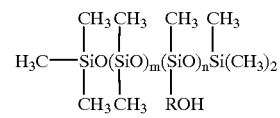

(m = 1–200, n = 2–200, R = lower alkylene group)

-continued

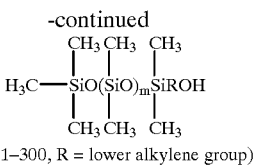
(m = 1–300, R = lower alkylene group)

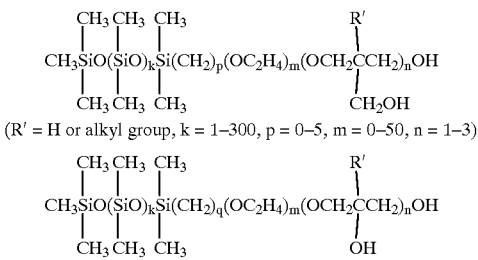

(4) Mercapto-modified polysiloxanes

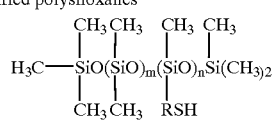
(m = 1–200, n = 2–200, R = lower alkylene group)

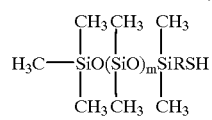
(m = 1–300, R = lower alkylene group)

(5) Carboxyl-modified siloxanes

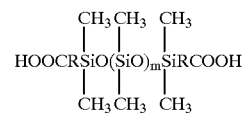
(m = 1–300, R = lower alkylene group)

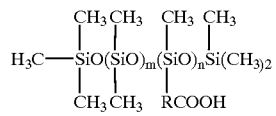
(m = 1–200, n = 2–200, R = lower alkylene group)

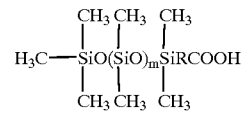
(m = 1–300, R = lower alkylene group)

The above-listed polysiloxane, each of which has an active-hydrogen-containing group, are examples of compounds preferred for use in the present invention, and in the present invention, the siloxane shall not be limited to these exemplified compounds. Not only the above-exemplified polysiloxanes but also polysiloxanes presently sold on the market and readily available from the market are, therefore, all usable in the present invention. Polysiloxanes particularly preferred in the present invention are those containing at least one hydroxyl group or amino group.

For the production of such a fluorine-containing polyurethane of present invention as described above (the term "fluorine-containing polyurethane" as used herein will hereinafter mean to also embrace such compounds as containing polysiloxane segment(s)), the above-described polysiloxane can be used in the form of a solution in an organic solvent, a suspension in water, or pellets of 100 wt. % solid content.

In the fluorine-containing polyurethane available from the use of $R_f$-containing diol according to the present invention, polyurethane molecular chains which are bonded via urethane fluorine-containing side chains represented by the formula (II) are bonded via $R_1$ and $R_2$ thereof to the backbone of the fluorine-containing polyurethane by means of urethane bonds (—NH—CO—O—) and/or urea bonds (NH—CO—NH—). Use of a diol provides a polyurethane, use of a diamine provides a polyurea, and combined use of a diol and an amine provides a polyurethane-polyurea.

The content of the fluorine-containing side chains in the polyurethane molecule may preferably range from 3 to 80 wt. % in terms of a fluorine content based on $R_f$ groups in the polyurethane molecule. A content lower than 3 wt. % leads to insufficient development of a function associated with surface energy based on the $R_f$ groups, while a content higher than 80 wt. % results in reductions in good properties inherent to polyurethane such as abrasion resistance and mechanical strength. Their contents outside the above-described range are, therefore, not preferred. Their content may preferably range from 5 to 50 wt. %, with a range of from 5 to 25 wt. % being more preferred.

The fluorine and silicon-containing polyurethane according to the present invention, which is available from the use of an $R_f$-containing one-end diol, a polysiloxane having at least one active-hydrogen-containing group in a molecule and the above-described another polyurethane component, is a polyurethane in which segments formed from a diisocyanate and segments formed from a diisocyanate are contained in the polyurethane backbone as in conventional polyurethanes, fluorine-containing side chains formed from a fluorine-containing diol presented by the formula (I) are bonded via $R_1$ and $R_2$ thereof to the backbone by means of urethane bonds and/or urea bonds, and polysiloxane segments formed from the polysiloxane are bonded to the backbone by means of urethane bonds and/or urea bonds.

The content of the polysiloxane segments in the polyurethane molecule may preferably be in such an amount that the siloxane content in the molecule ranges from 1 to 75 wt. %. A content lower than 1 wt. % leads to insufficient development of a function associated with surface energy based on the polysiloxane segments, while a content higher than 75 wt. % results in reductions in good properties inherent to polyurethane such as abrasion resistance and mechanical strength. Their contents outside the above-described range are, therefore, not preferred. Their content may preferably range from 3 to 50 wt. %, with a range of from 5 to 20 wt. % being more preferred.

The preferable fluorine content and polysiloxane segment content in the fluorine-containing polyurethane according to the present invention vary depending upon its application purpose, so that it is desired to obtain each fluorine-containing polyurethane with fluorine and polysiloxane segment contents suited for its application purpose.

The weight average molecular weight of the fluorine-containing polyurethane according to the present invention (as measured by GPC and calibrated against standard polystyrene) may range preferably from 5,000 to 500,000, more preferably from 30,000 to 150,000.

The fluorine-containing polyurethane, which is available from the $R_f$-containing diol of the present invention represented by the formula (I) and may optionally contain polysiloxane segments, is an excellent polyurethane having properties derived from $R_f$ groups, such as water repellency and oil repellency, anti-fouling property and non-tackiness, in addition to good properties inherent to polyurethanes such as high abrasion resistance, mechanical strength, flexibility, modulus of recoverable elasticity and chemical resistance.

Owing to these excellent characteristic features, the fluorine-containing polyurethane according to the present invention are useful as surface coating materials for various base materials, fiber coating materials, artificial leather, paints, and binders for magnetic recording media, and also for the production of thermoplastic molding or forming materials, industrial parts or components, sheets, films, tubes, and medical devices or equipment.

Fluorine-containing polyurethanes having branch chains or the like can also be obtained using conventionally known tri- or higher functional compounds in combination with the above-described diisocyanates, diols and diamines.

The present invention will hereinafter be described more specifically based on Examples and Comparative Examples. It should, however, be borne in mind that the present invention is not limited to or by these Examples. In the following Examples and Comparative Examples, all designations of "part" or "parts" and "%" are on weight basis unless otherwise specifically indicated.

EXAMPLE 1

[Synthesis of Fluorine-containing Diol (I-A)]

In a reaction vessel equipped with a stirrer, a thermometer, a nitrogen gas inlet tube and a reflux condenser and purged with nitrogen gas, isophorone diisocyanate (22.2 parts) was dissolved in ethyl acetate (50 parts). Under thorough stirring at 60° C., powdery 2-(perfluorooctyl)ethanol (46.4 parts) was gradually added. After completion of the addition, the isophorone diisocyanate and 2-(perfluorooctyl)ethanol were reacted at 80° C. for 3 hours, whereby a perfluoroalkyl-containing one-end isocyanate (A) was formed.

Diethanolamine (10.5 parts) was next mixed in ethyl acetate (10 parts) at temperatures not higher than 10° C. under stirring, and into the resulting solution, the reaction mixture with the compound (A) contained therein was added dropwise. With each dropwise addition of the reaction mixture with the compound (A) contained therein, occurrence of an exothermic reaction was observed. The dropwise addition was, therefore, effected such that the internal temperature did not exceed 20° C. As the reaction proceeded, the reaction mixture changed from a non-homogeneous solution into a homogeneous solution. Subsequent to completion of the dropwise addition, the reaction was allowed to continue for 2 hours at room temperature (25° C.)

After completion of the reaction, toluene was added to the reaction mixture to have the reaction product precipitated. The precipitate was collected by filtration, washed and then dried, whereby a while powdery product was obtained (yield: 95%).

The fluorine content of the powdery reaction product was measured by an ion-exchange chromatographic analyzer (manufactured by Yokogawa Hokushin Denki K.K.). Further, the melting point of the powdery reaction product was 132° C. Its hydroxyl number measured in accordance JIS K-0070 was 138 (mgKOH/g) (calculated: 142).

An infrared absorption spectrum of the reaction product is shown in FIG. 1. Characteristic bands (cm$^{-1}$) of individual atom groups determined from FIG. 1 are as follows:

Urethane (—O—CO—N—): 1,690, tertiary amido (—CO—N<): 1,650, amido (—CO—NH—): 1,390, 1,530, 1,500; N—H: 3,351; C=O of amido: 1,260; 1,3,5-substituted cyclohexane ring: 670, 705, 765 (methyl-substituted derivative); —CH$_2$—: 1,470, 2,850, 2,925; —CH$_3$; 1,460, 2,980; branch CH$_3$: 1,380; —OH: 3,410, C—F: 1,120, 1,210; —CF$_2$—: 1,150; —CF$_3$: 1,346.

From the above-described characteristic bands of the infrared absorption spectrum and the above-described hydroxyl number, the reaction production was confirmed to have the following chemical structure:

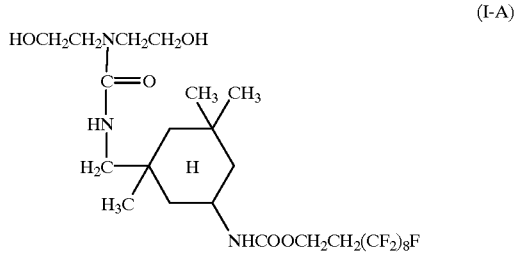

(I-A)

EXAMPLE 2

[Synthesis of Fluorine-containing Diol (I-B)]

A white powdery product of the below-described structure was obtained in a similar manner as in Example 1 except that in place of isophorone diisocyanate, 2,4-tolylene diisocyanate was used in the same equivalent amount.

The melting point of the product was 145° C. Its hydroxyl number was 148 (calculated: 151). Determination of its chemical structure was conducted in a similar manner as in Example 1. From characteristic bands of an infrared absorption spectrum, said characteristic bands being the same as those in Example 1 except for the replacement of the characteristic bands of the 1,3,5-substituted cyclohexane ring by characteristic bands of the 1,2,4-substituted benzene ring at 810–865, 675–730 and 835 cm$^{-1}$ (methyl-substituted derivative), and the hydroxyl number, the reaction product was confirmed to have the following structure:

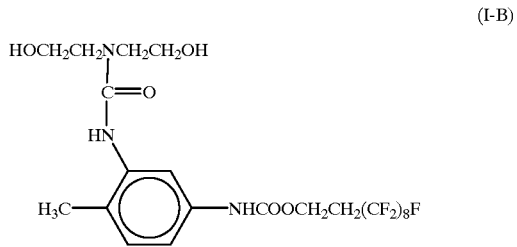

(I-B)

EXAMPLE 3

[Synthesis of Fluorine-containing Diol(I-C)]

A fluorine-containing diol (I-C) of the below-described formula was obtained as white powder in a similar manner as in Example 1 except that in place of diethanolamine and 2-(perfluoro-7-methyloctyl)ethanol, diethanolaminopropylamine and 2-(perfluorodecyl)ethanol were used in the same equivalent amounts, respectively.

The melting point of the product was 153° C. Its hydroxyl number was 115 (calculated: 118). From characteristic bands of an infrared absorption spectrum and the hydroxyl number, the reaction product was confirmed to have the following structure:

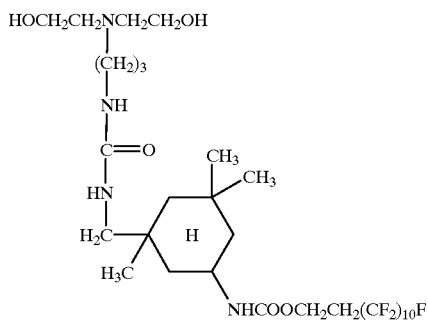
(I-C)

EXAMPLES 4–6

(Synthesis of Polyurethanes)

Figure 2:
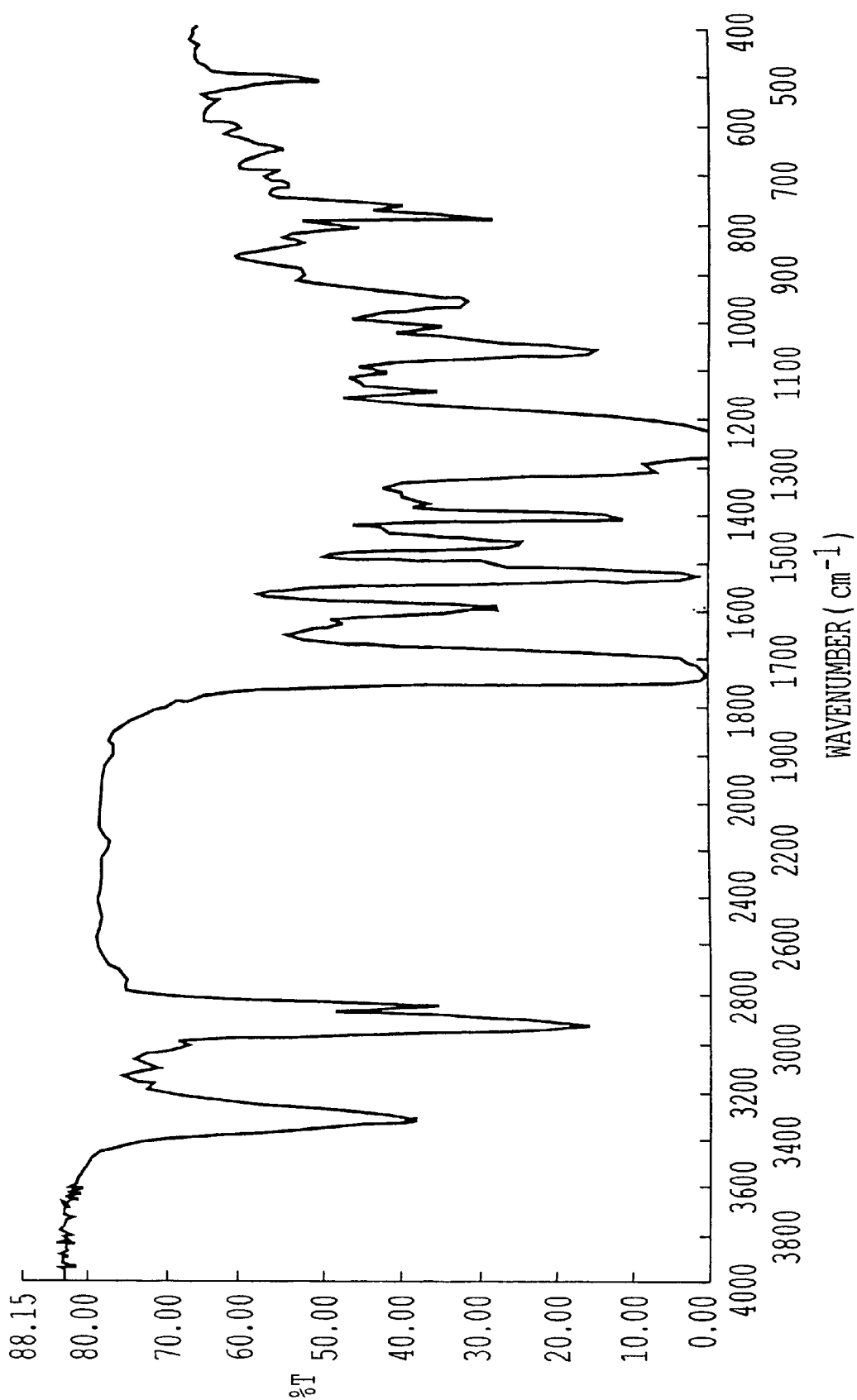
FIG. 2 is an infrared absorption spectrum of a fluorine-containing diol of Example 5.

In each of the Examples, the corresponding fluorine-containing diol (I-A, I-B or I-C), the corresponding fluorine-free polymer diol and the fluorine-free diol, all of which are shown in Table 1, were added into a reaction vessel equipped with a stirrer, a thermometer, a nitrogen gas inlet tube and a reflux condenser and purged with nitrogen gas. Dimethylformamide was added in an amount such that a reaction mixture to be finally obtained would have a solid content of 35%, whereby a homogeneous solution was obtained. The diisocyanate shown in Table 1 was then added. A reaction was conducted at 80° C. until a predetermined solution viscosity was reached, whereby a polyurethane according to the present invention was obtained. An infrared absorption spectrum of the fluorine-containing polyurethane of Example 5 is shown in FIG. 2.

COMPARATIVE EXAMPLES 1–4

(Synthesis of Polyurethanes)

In each of Comparative Examples 1–3, a fluorine-containing polyurethane was obtained in a similar manner as in Examples 4–6 by using the corresponding one of the following three fluorine-containing diols (I-A', I-B' and I-C') and also the corresponding polymer diol and the diol, both of which are shown in Table 2. Likewise, a still further polyurethane (Comparative Example 4) was obtained without using any fluorine-containing diol.

$HOCH_2CH_2C_4H_8CH_2CH_2OH$ (I-A')

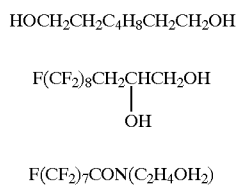
(I-B')

$F(CF_2)_7CON(C_2H_4OH_2)$ (I-C')

EXAMPLES 7–9

(Synthesis of Polyurethanes)

In each of the Examples, the corresponding one of the fluorine-containing diols (I-A, I-B, I-C) obtained in Examples 1–3, respectively, the corresponding one of the below-described polysiloxanes (II-A, II-B, II-C), the corresponding fluorine-free polymer diol shown in Table 3 and the fluorine-free diol shown in Table 3 were added into a reaction vessel equipped with a stirrer, a thermometer, a nitrogen gas inlet tube and a reflux condenser and purged with nitrogen gas. Dimethylformamide was added in an amount such that a reaction mixture to be finally obtained would have a solid content of 35%, whereby a homogeneous solution was obtained. The diisocyanate shown in Table 3 was then added in a predetermined equivalent amount. A reaction was conducted at 80° C. until a predetermined solution viscosity was reached, whereby a polyurethane according to the present invention was obtained.

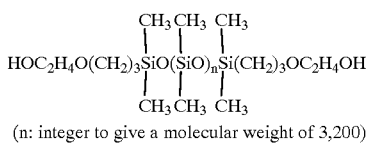
(II-A)

(n: integer to give a molecular weight of 3,200)

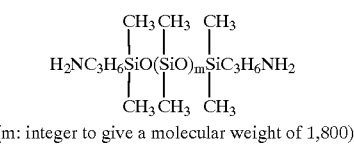
(II-B)

(m: integer to give a molecular weight of 1,800)

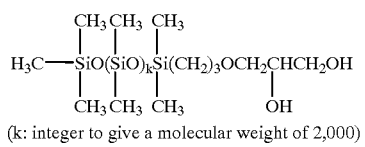
(II-C)

(k: integer to give a molecular weight of 2,000)

Comparative Examples 5–8

(Synthesis of Polyurethanes)

In each of Examples 5 and 6, a fluorine and silicon-containing polyurethane was obtained in a similar manner as in Examples 7–9 by using the corresponding one of the two fluorine-containing diols (I-A', I-B'), the corresponding polysiloxane shown in Table 4 and the diol shown in Table 4. In a similar manner, a further polyurethane (Comparative Example 7) was produced without using any fluorine-containing diol, and a still further polyurethane (Comparative Example 8) was produced without using any fluorine-containing diol and polysiloxane.

The fluorine content in the polyurethane of each of the Examples and Comparative Examples was measured using an ion-exchange chromatographic analyzer (manufactured by Yokogawa Hokushin Denki K.K.), while its polysiloxane segment content was measured in terms of siloxane content in accordance with the infrared spectrophotometric analysis method set out in JIS K0117. Further, its solution viscosity was measured at 25° C. by using a Brookfield Viscometer. Using GPC (manufactured by TOSOH CORPORATION) (column: "A-80M", trade name; manufactured by Showa Denko K.K.) and as a solvent, THF, its weight average molecular weight was determined in terms of a weight average molecular weight calibrated against standard polystyrene. Its physical properties were measured in accordance with JIS K6301. Further, its surface properties were measured by the below-described methods. The results of the above measurements are presented in Tables 1–4.

Contact angle

Measured using a contact angle meter manufactured by KYOWA INTERFACE SCIENCE CO., LTD.

Abrasion test

Following JIS K-7311, a film which had been formed by drying a solution of the polyurethane of each of Examples 4–9 and Comparative Examples 1–8 was bonded to a paperboard as a base material, and on a Taber abrader, an H-22 abrasive wheel was driven 100 revolutions under a load of 1 kg. An abrasion wear was measured.

Peel strength

A solution of each polyurethane was coated on a polyester film (PET) to give a dry coat weight of 1 µm, whereby a film was formed. An acrylic adhesive tape of 20 mm in width (product of Sekisui Chemical Co., Ltd.) was adhered under pressure onto the film by a rubber roller the own weight of which was 2 kg. One hour later, the peel strength was measured.

Coefficient of static friction

Measured using a surface property tester manufactured by Shinto Scientific Co., Ltd.

TABLE 1

|  | Ex. 4 | Ex. 5 | Ex. 6 |
| --- | --- | --- | --- |
| Composition of PU raw materials | | | |
| Fluorine-containing diol (i) | I-A | I-B | I-C |
| Polymer diol (ii) | POTMG (*1) | PCDO (*2) | PCLPO (*3) |
| Diol (iii) | 1,4-BG (*4) | *4 | *4 |
| i/ii/iii (weight ratio) | 2.5/12.5/1 | 6/15/1 | 12/10/1 |
| Diisocyanate | MDI (*5) | *5 | *5 |
| NCO/OH (molar ratio) | 1.02/1.00 | 1.02/1.00 | 1.02/1.00 |
| PU properties | | | |
| Solution viscosity (35% concentration, dPa.s) | 240 | 320 | 200 |
| Weight average m.w. | 67,000 | 78,000 | 56,000 |
| Fluorine content in PU (%) | 6 | 12 | 20 |
| Physical properties of PU | | | |
| 100% modulus (20° C., MPa) | 3.6 | 6.6 | 7.1 |
| 100% modulus (0° C., MPa) | 9.1 | 9.8 | 13.2 |
| 100% modulus (−20° C., MPa) | 18.5 | 21 | 27 |
| Breaking strength (20° C., MPa) | 52 | 56 | 49 |
| Breaking extension (20° C., %) | 560 | 545 | 480 |
| PU surface properties | | | |
| Contact angle (degrees) | | | |
| Water | 108 | 110 | 112 |
| Dodecane | 68 | 70 | 71 |
| Abrasion wear (mg) | 90 | 72 | 55 |
| Peel strength (N/m) | 34.3 | 24 | 19.6 |
| Coefficient of static friction (µ) | 0.26 | 0.19 | 0.12 |

TABLE 2

|  | Comp. Ex. 1 | Comp. Ex. 2 | Comp. Ex. 3 | Comp. Ex. 4 |
| --- | --- | --- | --- | --- |
| Composition of PU raw materials | | | | |
| F-containing diol (i) | I-A' | I-B' | I-C' | — |
| Polymer diol (ii) | *1 | *2 | *3 | *3 |
| Diol (iii) | *4 | *4 | *4 | *4 |
| i/ii/iii (wt. ratio) | 3.3/6.7/1 | 3/7/1 | 10/10/1 | 0/15/1 |
| Diisocyanate | *5 | *5 | *5 | *5 |
| NCO/OH (molar ratio) | 1.02/1.00 | 1.02/1.00 | 1.02/1.00 | 1.02/1.00 |
| PU properties | | | | |
| Solution viscosity (35% conc., dPa.s) | 300 | 280 | 220 | 350 |
| Weight average m.w. | 69,000 | 70,000 | 63,000 | 82,000 |
| F content in PU (%) | 12 | 15 | 23 | 0 |
| Physical properties of PU | | | | |
| 100% modulus (20° C., MPa) | 19.4 | 18.1 | 21 | 5.6 |
| 100% modulus (0° C., MPa) | 36 | 28.1 | — | 6.8 |
| 100% modulus (−20° C., MPa) | 49 | 44 | — | 14.2 |
| Breaking strength (20° C., MPa) | 76 | 56 | 45 | 57 |
| Breaking extension (20° C., %) | 360 | 285 | 230 | 400 |
| PU surface properties | | | | |
| Contact angle (degrees) | | | | |
| Water | 105 | 108 | 112 | 73 |
| Dodecane | 38 | 65 | 70 | 10 |
| Abrasion wear (mg) | 180 | 90 | 65 | 310 |
| Peel strength (N/m) | 37.3 | 28 | 18.3 | 295 |
| Coefficient of static friction (µ) | 0.25 | 0.18 | 0.12 | 0.62 |

TABLE 3

|  | Ex. 7 | Ex. 8 | Ex. 9 |
| --- | --- | --- | --- |
| Composition of PU raw materials | | | |
| Fluorine-containing diol (i) | I-A | I-B | I-C |
| Polysiloxane (ii) | II-A | II-B | II-C |
| Polymer diol (iii) | *1 | *2 | *3 |
| Diol (iv) | *4 | *4 | *4 |
| i/ii/iii/iv (wt. ratio) | 7/3/20/1 | 12/8/10/1 | 30/10/10/1 |
| Diisocyanate | *5 | *5 | *5 |
| NCO/OH (molar ratio) | 1.02/1.00 | 1.02/1.00 | 1.02/1.00 |
| PU properties | | | |
| Solid content (%) | 35 | 35 | 35 |
| Solution viscosity (25° C., dPa.s) | 250 | 310 | 210 |
| Weight average m.w. | 68,000 | 72,000 | 57,000 |
| Fluorine content (%) | 7 | 13 | 19 |
| Siloxane content (%) | 8 | 18 | 14 |
| Physical properties of PU | | | |
| 100% modulus (MPa) 20° C. | 4.2 | 5.9 | 7.2 |
| 100% modulus (MPa) 0° C. | 8.1 | 11.5 | 15.6 |
| 100% modulus (MPa) −20° C. | 17.3 | 19 | 25 |
| Breaking strength (MPa) 20° C. | 48 | 52 | 50 |
| Breaking extension (%) 20° C. | 510 | 500 | 520 |

TABLE 3-continued

|  | Ex. 7 | Ex. 8 | Ex. 9 |
|---|---|---|---|
| PU surface properties | | | |
| Contact angle (degrees) | | | |
| Water | 108 | 110 | 112 |
| Dodecane | 67 | 70 | 71 |
| Abrasion wear mg | 65 | 53 | 45 |
| Peel strength N/m | 18 | 15 | 10 |
| Coefficient of static friction $\mu$ | 0.12 | 0.1 | 0.09 |

TABLE 4

|  | Comp. Ex. 5 | Comp. Ex. 6 | Comp. Ex. 7 | Comp. Ex. 8 |
|---|---|---|---|---|
| Composition of PU raw materials | | | | |
| F-containing diol (i) | I-A' | I-B' | — | — |
| Polysiloxane (ii) | — | II-A | II-C | — |
| Polymer diol (ii) | *1 | *2 | *3 | *3 |
| Diol (iii) | *4 | *4 | *4 | *4 |
| i/ii/iii/iv (wt. ratio) | 3.3/0/6.7/1 | 7/3/20/1 | 0/3/21/1 | 0/0/15/1 |
| Diisocyanate | *5 | *5 | *5 | *5 |
| NCO/OH (molar ratio) | 1.02/1.00 | 1.02/1.00 | 1.02/1.00 | 1.02/1.00 |
| PU properties | | | | |
| Solid content (%) | 35 | 35 | 35 | 35 |
| Solution viscosity (25° C., dPa.s) | 300 | 290 | 210 | 350 |
| Weight average m.w. | 71,000 | 68,000 | 57,000 | 82,000 |
| Fluorine content (%) | 10 | 15 | 0 | 0 |
| Siloxane content (%) | 0 | 9 | 14 | 0 |
| Physical properties of PU | | | | |
| 100% modulus (MPa) 20° C. | 19.4 | 17.5 | 3.5 | 5.6 |
| 100% modulus (MPa) 0° C. | 36 | 27 | 5.7 | 6.8 |
| 100% modulus (MPa) −20° C. | 49 | 45 | 9.3 | 14.2 |
| Breaking strength (%) 20° C. | 76 | 51 | 15 | 57 |
| Breaking extension (%) 20° C. | 360 | 450 | 450 | 400 |
| PU surface properties | | | | |
| Contact angle (degrees) | | | | |
| Water | 105 | 110 | 100 | 73 |
| Dodecane | 38 | 70 | 12 | 10 |
| Abrasion wear mg | 180 | 53 | 20 | 310 |
| Peel strength N/m | 37.3 | 15 | 0 | 295 |
| Coefficient of static friction $\mu$ | 0.12 | 0.1 | 0.09 | 0.62 |

(Note) (common to Table 1 to Table 4)
*1 POTMG: polyoxytetramethylene glycol, m.w.: 2000
*2 PCDO: polycarbonatediol, m.w.: 2000
*3 PCLPO: polycaprolactonepolyol, m.w.: 2000
*4 1,4-BG: 1,4-butylene glycol
*5 MDI: 4,4'-methylenebis (phenyl isocyanate)
PU: polyurethane Further, fluorine-containing diols were obtained in a similar manner as in Example 1 except that the below-described fluorine-containing alcohols 1–8 were used, respectively, in lieu of 2-(perfluorooctyl)ethanol. Using the thus-obtained fluorine-containing diols, the corresponding fluorine-containing (polysiloxane-containing) polyurethanes were also obtained in a similar manner as in Examples 4 and 7. The resultant fluorine-containing (polysiloxane-containing) polyurethanes showed excellent physical properties like the fluorine-containing (polysiloxane-containing) polyurethanes of Examples 4 and 7.

Used fluorine-containing alcohols

1. $F(CF_2)_m(CH_2)_nOH$ (m = 6, n = 6)

2. $(CF_3)_2CF(CF_2)_m(CH_2)_nOH$ (m = 6, n = 2)

3. $F(CF_2)_mCH=CH(CH_2)_nOH$ (m = 8, n = 2)

4. $F(CF_2)_mCH_2CHI(CH_2)_nOH$ (m = 10, n = 2)

5. $(CF_3)_2CF(CF_2)_mCH_2CHI(CH_2)_nOH$ (m = 4, n = 2)

6. $H(CF_2)_m(CH_2)_nOH$ (m = 8, n = 1)

7. $F(CF_2)_mO\text{—}C_6H_4\text{—}(CH_2)_nOH$ (m = 8, n = 2)

8. $(CF_3)_2CF(CF_2)_mO\text{—}C_6H_4\text{—}(CH_2)_nOH$ (m = 6, n = 2)

What is claimed is:

1. A fluorine-containing diol represented by the following formula (I):

$$R_f\text{—}X\text{—}Y\text{—}\underset{O}{\overset{\parallel}{C}}\text{—}\underset{H}{\overset{|}{N}}\text{—}R_3\text{—}\underset{H}{\overset{|}{N}}\text{—}\underset{O}{\overset{\parallel}{C}}\text{—}Z\text{—}N\begin{Bmatrix}R_1\text{—}OH\\R_2\text{—}OH\end{Bmatrix} \quad (I)$$

wherein $R_f$ represents a perfluoroalkyl or perfluoroalkenyl group having 1 to 20 carbon atoms; X represents a substituted or unsubstituted alkylene group having 1 to 10 carbon atoms, a substituted or unsubstituted alkenylene group represented by —CH=CH—$(CH_2)_n$— in which n stands for an integer of from 1 to 10, or

in which n stands for an integer of from 0 to 6; Y represents a direct bond, —O—, —NH—, or —$R_0$—NH— in which $R_0$ is an alkylene group having 1 to 6 carbon atoms; Z represents a direct bond or —N(R')R— in which R is an alkylene group having 1 to 20 carbon atoms and R' is a hydrogen atom or an alkyl group having 1 to 6 carbon atoms; $R_1$ and $R_2$ each independently represent a divalent organic group; and $R_3$ represents a residual group of an aliphatic, alicyclic or aromatic diisocyanate.

2. A process for the preparation of a fluorine-containing diol represented by the formula (I) as defined in claim 1, which comprises reacting a fluorine-containing compound, which has an $R_f$ group and an active-hydrogen-containing group, with a diisocyanate at an NCO/OH ratio of approximately 2, and then reacting a resulting fluorine-containing group, which contains one free isocyanate group in a molecule, with a dialkanolamine at a temperature not higher than 50° C.

3. A process according to claim 2, wherein said fluorine-containing compound having said $R_f$ group and said active-hydrogen-containing group is at least one fluorine-containing group selected from the group consisting of the following compounds:

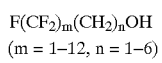

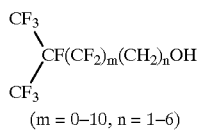

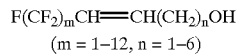

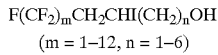

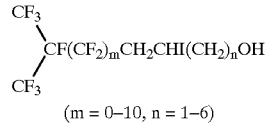

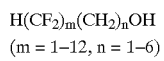

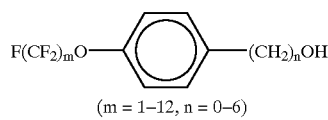

-continued

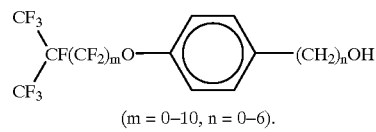

4. A process according to claim 2, wherein said dialkanolamine is represented by the following formula:

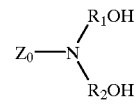

wherein $R_1$ and $R_2$ have the same meanings as defined above, and $Z_0$ represents H or an alkylamino group having 1 to 20 carbon atoms and a single primary or secondary amino group at an end thereof.

5. A fluorine-containing polyurethane obtained by reacting a fluorine-containing diol represented by the formula (I) as defined in claim 1, an aliphatic, aromatic or alicyclic diisocyanate, and an aliphatic, aromatic or alicyclic diol and/or a diamine, and optionally, a chain extender; said polyurethane having fluorine-containing side chains, which are represented by the following formula (II):

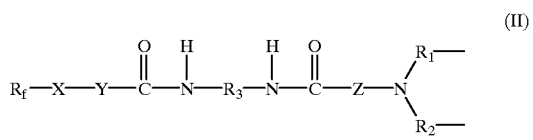

wherein $R_1$ to $R_3$, $R_f$, X, Y and Z have the same meanings as defined claim 1 and which are bonded via $R_1$ and $R_2$ thereof to a backbone of said polyurethane by means of urethane bonds and/or urea bonds, at a content such that said polyurethane has a fluorine content of from 3 to 80 wt. %; and said polyurethane having a weight average molecular weight of from 5,000 to 500,000.

6. A fluorine-containing polyurethane according to claim 5, wherein said weight average molecular weight ranges from 50,000 to 150,000.

7. A fluorine-containing polyurethane according to claim 5, wherein said fluorine content ranges from 5 to 50 wt. %.

8. A fluorine-containing polyurethane according to claim 5, wherein said fluorine content ranges from 5 to 25 wt. %.

9. A fluorine-containing polyurethane according to claim 5, further comprising 1 to 75 wt. % of polysiloxane segments derived from a polysiloxane having at least one active-hydrogen-containing group.

10. A fluorine-containing polyurethane according to claim 9, wherein a content of said polysiloxane segments ranges from 3 to 50 wt. %.

11. A fluorine-containing polyurethane according to claim 9, wherein a content of said polysiloxane segments ranges from 3 to 20 wt. %.

12. A fluorine-containing polyurethane according to claim 9, wherein said active-hydrogen-containing group of said polysiloxane is a hydroxyl group or an amino group.

13. A process for the production of a fluorine-containing polyurethane as defined in claim 5, which comprises reacting a fluorine-containing diol represented by the formula (I) as defined in claim 1, a diisocyanate, and a diol other than said fluorine-containing diol and/or a diamine, and optionally a chain extender.

14. A process according to claim 13, wherein said fluorine-containing diol represented by the formula (I) as defined in claim 1 is used in an amount such that a content of fluorine in said polyurethane falls within a range of from 3 to 80 wt. %.

15. A process according to claim 13, wherein a polysiloxane having at least one active-hydrogen-containing group is reacted further in an amount such that a content of polysiloxane segments in said polyurethane falls within a range of from 1 to 75 wt. %.

16. A process according to claim 15, wherein said active-hydrogen-containing group of said polysiloxane is a hydroxyl group or an amino group.

* * * * *